United States Patent
Yoshitomo et al.

(10) Patent No.: US 7,456,323 B2
(45) Date of Patent: Nov. 25, 2008

(54) 1,3-BIS(3-FORMYL-4-HYDROXYPHENYL)ADAMANTANES AND POLYNUCLEAR POLYPHENOLS DERIVED THEREFROM

(75) Inventors: Akira Yoshitomo, Wakayama (JP); Tatsuya Iwai, Wakayama (JP); Kentaro Watanabe, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 11/915,829

(22) PCT Filed: Jun. 13, 2006

(86) PCT No.: PCT/JP2006/311824

§ 371 (c)(1),
(2), (4) Date: Dec. 14, 2007

(87) PCT Pub. No.: WO2006/134909

PCT Pub. Date: Dec. 21, 2006

(65) Prior Publication Data

US 2008/0242896 A1    Oct. 2, 2008

(30) Foreign Application Priority Data

Jun. 17, 2005  (JP) .............................. 2005-178399
Mar. 30, 2006  (JP) .............................. 2006-093728

(51) Int. Cl.
*C07C 45/00*     (2006.01)
*C07C 47/00*     (2006.01)
*C07C 39/00*     (2006.01)

(52) U.S. Cl. .................. 568/436; 568/439; 568/718
(58) Field of Classification Search ................ 568/435, 568/439, 718
See application file for complete search history.

(56) References Cited

U.S. PATENT DOCUMENTS 3,594,427 A    7/1971    Moore

FOREIGN PATENT DOCUMENTS

| JP | 10-130371 | 5/1998 |
| JP | 2000-143566 | 5/2000 |
| JP | 2003-212987 | 7/2003 |
| JP | 2003-306460 | 10/2003 |
| JP | 2005-148275 | 6/2005 |

*Primary Examiner*—Sikarl A Witherspoon
(74) *Attorney, Agent, or Firm*—Knobbe, Martens Olson & Bear LLP

(57) ABSTRACT

A new 1,3-bis(3-formyl-4-hydroxyphenyl)adamantane, which provides a material offering excellent properties such as heat resistance and mechanical strength for use as an intermediate material for adamantanebisphenol derivatives or use in photosensitive resist materials, epoxy resins and other synthetic resins, thermosensitive recording materials, and the like, can be obtained through an industrial process in an easy manner at a good yield and high purity by producing a Schiff base from a 1,3-bis(4-hydroxyphenyl)adamantane by causing it to react with a hexamethylenetetramine or other substance in the presence of an acid, and then hydrolyzing the obtained Schiff base using an acid. A new polynuclear polyphenol is also provided that may be derived from the same.

5 Claims, No Drawings

1,3-BIS(3-FORMYL-4-HYDROXYPHENYL)ADAMANTANES AND POLYNUCLEAR POLYPHENOLS DERIVED THEREFROM

This application is the U.S. National Phase under 35 U.S.C. §371 of International Application PCT/JP2006/311824, filed Jun. 13, 2006, which claims priority to Japanese Patent Application No. 2005-178399, filed Jun. 17, 2005 and Japanese Patent Application No. 2006-093728, filed Mar. 30, 2006. The International Application was published under PCT Article 21(2) in a language other than English.

TECHNICAL FIELD

The present invention relates to a new 1,3-bis(3-formyl-4-hydroxyphenyl)adamantane as well as a new polynuclear polyphenol that may be derived from the same.

These compounds are useful as intermediate materials for adamantanebisphenol derivatives, materials for photosensitive resist materials, materials and hardeners for epoxy resins, color developing agents and discoloration preventing agents used in thermosensitive recording materials, and materials for bactericides, fungicides and antioxidants, and the like. The polynuclear polyphenol proposed by the present invention is particularly useful as a material for photosensitive resist materials.

PRIOR ART

Adamantanebisphenols that have traditionally been known include 1,3-bis(4-hydroxyphenyl)-5,7-dimethyladamantane synthesized by using 1,3-dibromo-5,7-dimethyladamantane and phenol as materials (U.S. Pat. No. 3,594,427), 1,3-bis(4-hydroxyphenyl)adamantane synthesized by using 1,3-adamantanediol and phenol as materials (Japanese Patent Laid-open No. 2000-143566), 1,3-bis(4-hydroxy substituted phenyl)adamantane synthesized by using 1,3-adamantanediol and alkyl substituted phenol as materials (Japanese Patent Laid-open No. 2003-306460), and 2,2-bis(4-hydroxyphenyl)adamantane synthesized by using 2-adamantanone and phenol as materials (Japanese Patent Laid-open No. Hei 10-130371), among others. However, the recent demand for a diverse range of substances offering higher performance for use as materials for photosensitive resist materials, materials and hardeners for epoxy resins, and color developing agents and discoloration preventing agents used in thermosensitive recording materials, among others, is giving rise to a need for adamantanebisphenols of various chemical structures. However, the industry has so far known no adamantanebisphenol having a chemical structure where a formyl group offering high reactivity is bonded with the phenyl ring of the hydroxyphenyl group bonded to position 1,3 of the adamantane ring. A compound having such chemical structure has in its molecule a formyl group offering high reactivity and is therefore expected to be useful for the purpose of synthesizing various derivatives of adamantanebisphenol with ease. Similarly, no compound has been known that has a chemical structure where a bis(hydroxyphenyl)methyl group is further bonded with the phenyl ring of the hydroxyphenyl group bonded to position 1,3 of the adamantane ring. A compound having such chemical structure has in one molecule at least six aromatic hydroxyl groups in addition to the adamantane ring offering excellent heat resistance, and is therefore expected to provide a new performance material for use in photosensitive resist materials, etc.

Literature 1: U.S. Pat. No. 3,594,427
Literature 2: Japanese Patent Laid-open No. 2000-143566
Literature 3: Japanese Patent Laid-open No. 2003-306460
Literature 4: Japanese Patent Laid-open No. Hei 10-130371

SUMMARY OF THE INVENTION

Problems to be Solved by the Invention

In consideration of the above, one object of the present invention is to provide an adamantanebisphenol compound having a chemical structure where a formyl group offering high reactivity is bonded with the phenyl ring of the hydroxyphenyl group bonded to position 1,3 of the adamantane ring, as well as a method of producing the same that can be used favorably in industrial applications. Another object of the present invention is to provide a polynuclear polyphenol having a chemical structure where a bis(hydroxyphenyl)methyl group is further bonded with the phenyl ring of the hydroxyphenyl group bonded to position 1,3 of the adamantane ring, as well as a method of producing the same that can be used favorably in industrial applications.

Means for Solving the Problems

After studying diligently to achieve the aforementioned objects, the inventors found that a compound having a chemical structure where position 3 of the phenyl ring of the hydroxyphenyl group attached to each of the two ends of a 1,3-bis(4-hydroxyphenyl)adamantane is substituted by a formyl group would offer excellent reactivity due to the substituting formyl group and ultimately help achieve the aforementioned object. Based on these findings, the inventors completed the present invention.

To be specific, the present invention provides a 1,3-bis(3-formyl-4-hydroxyphenyl)adamantane expressed by general formula (1) below.

[Chemical 1]

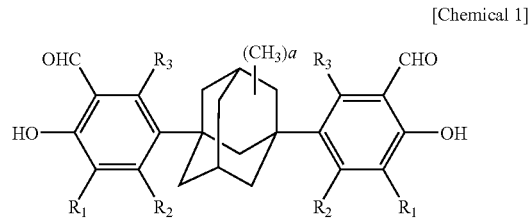

General Formula (1)

(wherein a represents an integer of 0 to 2, while $R_1$, $R_2$ and $R_3$ each represent independently a hydrogen atom or alkyl group with 1 to 4 carbon atoms)

A compound having such chemical structure can be obtained through an industrial process in an easy manner at a good yield and high purity by generating a Schiff base from a 1,3-bis(4-hydroxyphenyl)adamantane by causing it to react with a hexamethylenetetramine or other substance in the presence of an acid, and then hydrolyzing the obtained Schiff base using an acid.

The inventors also studied diligently regarding polynuclear polyphenols in relation to the other object of the present invention, and found that the aforementioned object could be achieved by a polynuclear polyphenol having a chemical structure where a bis(hydroxyphenyl)methyl group was bonded to position 3 of the phenyl ring of the hydroxyphenyl group attached to each of the two ends of a 1,3-bis(4-hydroxyphenyl)adamantane, and that a compound having such chemical structure could be produced easily by using the aforementioned 1,3-bis(3-formyl-4-hydroxyphenyl)adamantane as a material. Based on these findings, the inventors completed the present invention.

To be specific, in another aspect the present invention provides a polynuclear polyphenol expressed by general formula (2) below.

[Chemical 2]

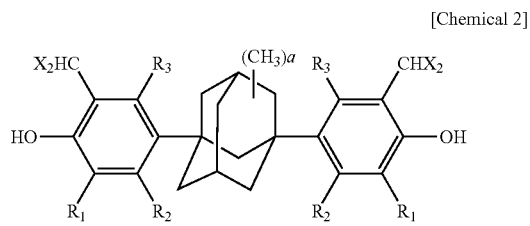

General Formula (2)

(wherein a, $R_1$, $R_2$ and $R_3$ are the same as in general formula (1), while X represents a hydroxyphenyl group expressed by general formula (3) below; in general formula (3), R represents an alkyl group with 1 to 4 carbon atoms or cycloakyl group with 5 to 7 carbon atoms, while b is an integer of 1 to 3 and c is an integer of 0 to 4, and if c is between 2 and 4, all Rs may be either identical or different, proviso that $1 \leq b+c \leq 5$).

[Chemical 3]

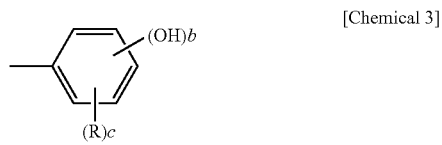

General Formula (3)

A compound having such chemical structure can be obtained through an industrial process in an easy manner at a good yield and high purity by, for example, causing a 1,3-bis (3-formyl-4-hydroxyphenyl)adamantane expressed by general formula (1) above to react with a phenol in the presence of an acid catalyst.

Effects of the Invention

The new 1,3-bis(3-formyl-4-hydroxyphenyl)adamantane proposed by the present invention is a bisphenol where the hydroxy phenyl group bonded to position 1,3 of the adamantane ring is substituted by a formyl group offering high reactivity, and an adamantane according to the above can be used as an intermediate material to synthesize various derivatives of adamantanebisphenol in an easy manner. In addition, such adamantane is expected to improve heat resistance, mechanical strength and various other performance properties if used as a material for photosensitive resist materials, material or hardener for epoxy resins and other synthetic resins, or color developing agent, discoloration preventing agent or other additive used in thermosensitive recording materials.

On the other hand, the new polynuclear polyphenol serving the other object of the present invention has a chemical structure where each molecule has at least six aromatic hydroxyl groups as a result of a bis(hydroxyphenyl)methane group substituting the hydroxyphenyl group bonded to position 1,3 of the adamantane ring. When such polynuclear polyphenol is used as a material or additive for photosensitive resists, therefore, improved resolution and other desirable properties can be expected. When used as a material or hardener for epoxy resins and other synthetic resins, or developing agent, discoloration preventing agent or other additive used in thermosensitive recording materials, such polynuclear polyphenol will likely improve heat resistance, flexibility, water resistance and various other performance properties.

BEST MODE FOR CARRYING OUT THE INVENTION

The new 1,3-bis(3-formyl-4-hydroxyphenyl)adamantane proposed by the present invention is expressed by general formula (1) below.

[Chemical 4]

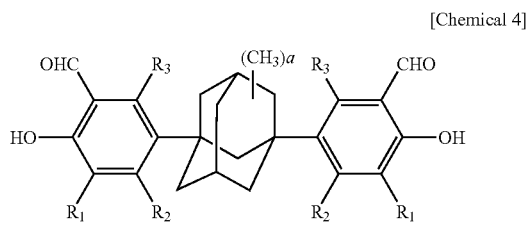

General Formula (1)

In the 1,3-bis(3-formyl-4-hydroxyphenyl)adamantane expressed by general formula (1) above, a represents an integer of 0 to 2, while $R_1$, $R_2$ and $R_3$ each represent independently a hydrogen atom or alkyl group with 1 to 4 carbon atoms. Among the possible combinations satisfying the above conditions, a compound where $R_1$ is an alkyl group and at least one of $R_2$ and $R_3$ is a hydrogen atom is preferable, while a compound where both $R_2$ and $R_3$ are a hydrogen atom or only $R_2$ is a hydrogen atom is more preferable. Also, a should preferably be 0.

Specific examples of the alkyl group with 1 to 4 carbon atoms to constitute $R_1$, $R_2$ and $R_3$ include, among others, a methyl group, ethyl group, propyl group and butyl group. The propyl group or butyl group may have a structure of straight chain or branched chain.

Accordingly, specific examples of the 1,3-bis(3-formyl-4-hydroxyphenyl)adamantane proposed by the present invention include the following, among others:

1,3-bis(3-formyl-5-methyl-4-hydroxyphenyl)adamantane expressed by the formula below

[Chemical 5]

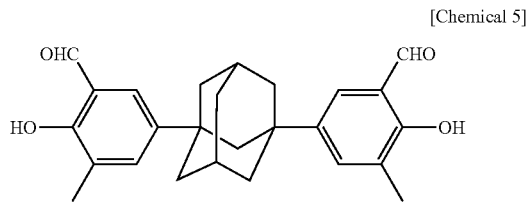

1,3-bis(3-formyl-5-isopropyl-4-hydroxyphenyl)adamantane expressed by the formula below

[Chemical 6]

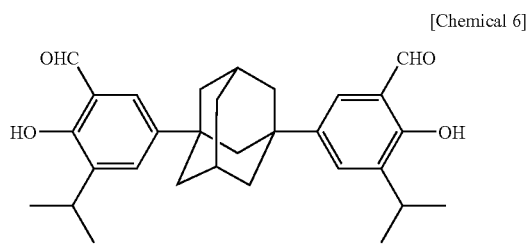

1,3-bis(3-formyl-4-hydroxyphenyl)adamantane,
1,3-bis(3-formyl-5-ethyl-4-hydroxyphenyl)adamantane,
1,3-bis(3-formyl-5-t-butyl-4-hydroxyphenyl)adamantane, 1,3-bis(3-formyl-5-n-propyl-4-hydroxyphenyl)adamantane,
1,3-bis(3-formyl-5-sec-butyl-4-hydroxyphenyl)adamantane,
1,3-bis(3-formyl-5-isobutyl-4-hydroxyphenyl)adamantane,
1,3-bis(3-formyl-5-n-butyl-4-hydroxyphenyl)adamantane,
1,3-bis(3-formyl-2,5-dimethyl-4-hydroxyphenyl)adamantane,
1,3-bis(2-methyl-3-formyl-5-isopropyl-4-hydroxyphenyl)adamantane,
1,3-bis(3-formyl-5-methyl-4-hydroxyphenyl)-4-methyladamantane,
1,3-bis(3-formyl-5-isopropyl-4-hydroxyphenyl)-4-methyladamantane, and
1,3-bis(3-formyl-5-isopropyl-4-hydroxyphenyl)-5,7-dimethyladamantane The 1,3-bis(3-formyl-4-hydroxyphenyl)adamantane expressed by general formula (1) above as proposed by the present invention is not limited in any way in terms of how it should be produced. A preferred method, however, is one where such adamantane can be obtained through an industrial process in an easy manner at a good yield and high purity by producing a Schiff base from a 1,3-bis(4-hydroxyphenyl)adamantane by causing it to react with a hexamethylenetetramine or other substance in the presence of an acid, and then hydrolyzing the obtained Schiff base using an acid.

The 1,3-bis(4-hydroxyphenyl)adamantane used as a material under the present invention is expressed by general formula (5) below.

[Chemical 7]

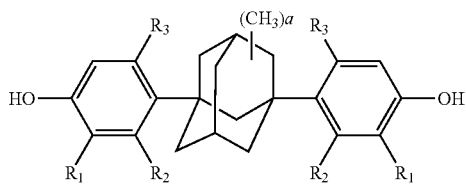

General Formula (5)

In the formula, a, $R_1$, $R_2$ and $R_3$ are the same as in general formula (1). In other words, specific examples of the aforementioned 1,3-bis(4-hydroxyphenyl)adamantane include the following, among others:

1,3-bis(3-methyl-4-hydroxyphenyl)adamantane,
1,3-bis(4-hydroxyphenyl)adamantane,
1,3-bis(3-isopropyl-4-hydroxyphenyl)adamantane,
1,3-bis(3-ethyl-4-hydroxyphenyl)adamantane,
1,3-bis(3-t-butyl-4-hydroxyphenyl)adamantane,
1,3-bis(3-n-propyl-4-hydroxyphenyl)adamantane,
1,3-bis(3-sec-butyl-4-hydroxyphenyl)adamantane,
1,3-bis(3-isobutyl-4-hydroxyphenyl)adamantane,
1,3-bis(3-n-butyl-4-hydroxyphenyl)adamantane,
1,3-bis(2,5-dimethyl-4-hydroxyphenyl)adamantane,
1,3-bis(2-methyl-5-isopropyl-4-hydroxyphenyl)adamantane,
1,3-bis(3-methyl-4-hydroxyphenyl)-4-methyladamantane,
1,3-bis(3-methyl-4-hydroxyphenyl)-5,7-dimethyladamantane,
1,3-bis(3-isopropyl-4-hydroxyphenyl)-4-methyladamantane, and
1,3-bis(3-isopropyl-4-hydroxyphenyl)-5,7-dimethyladamantane Possible methods to produce the 1,3-bis(3-formyl-4-hydroxyphenyl)adamantane proposed by the present invention include the Duff reaction and Reimer-Tiemann reaction. Among these, use of the Duff reaction is preferred. For example, the aforementioned 1,3-bis(4-hydroxyphenyl)adamantane is used as a material and this material is caused to react with a hexamethylenetetramine in the presence of an acid such as trifluoroacetic acid to produce a Schiff base, and then the produced Schiff base is hydrolyzed under an acid condition, after which a formyl group is introduced. An example of the reaction formula of this process is given below.

[Chemical 8]

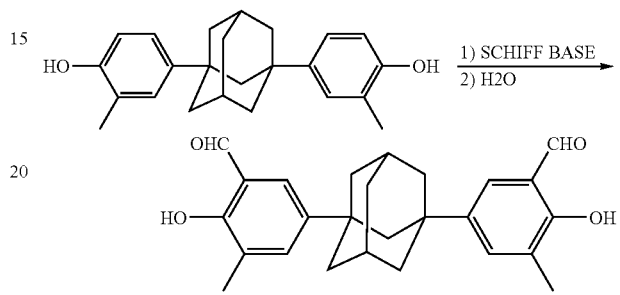

The ratio of 1,3-bis(4-hydroxyphenyl)adamantane and hexamethylenetetramine should be in a range of 2:1 to 5:1, or preferably in a range of 2.5:1 to 3.5:1, as the mol ratio of the base such as hexamethylenetetramine to the 1,3-bis(4-hydroxyphenyl)adamantane. Also, an acid is used in the aforementioned reaction. This acid may be boric acid, sodium hydrogen phosphate or other inorganic weak acid, or acetic acid, trifluoroacetic acid, formic acid or other carbonic acid.

Among these acids, acetic acid or trifluoroacetic acid is preferable because they lead to faster reaction and provide greater reaction selectivity, and these acids also function as a solvent. The amount of acid varies depending on the type of acid used and it is not possible to set a specific value. Normally, however, the amount of acid should be in a range of 2 to 50 times by mol, or preferably in a range of 10 to 30 times by mol, with respect to 1 mol of the material 1,3-bis(4-hydroxyphenyl)adamantane.

A reaction solvent may or may not be used in the reaction. Reaction solvents that can be used favorably include methanol and other lower aliphatic alcohols, toluene and other aromatic hydrocarbons, and tetrahydrofuran and other ethers. The amount of reaction solvent can be adjusted to, for example, a range of 5 to 50 percent by weight with respect to the material 1,3-bis(4-hydroxyphenyl)adamantane.

The reaction temperature is normally in a range of 50 to 150° C., or preferably in a range of 80 to 100° C. Under a temperature condition in these ranges, the reaction normally completes in around 5 to 40 hours.

Next, the produced Schiff base is hydrolyzed in an acidic atmosphere. The hydrolysis reaction should normally complete after an appropriate amount of water has been added to the aforementioned reaction solution and the reaction mixture is caused to react over a period of approx. 0.5 to 5 hours under agitation while maintaining the temperature in a range of 40 to 100° C., or preferably in a range of 60 to 80° C.

After the reaction has ended, an appropriate amount of aqueous sodium hydroxide solution or other alkali water is added to the obtained reaction mixture in order to neutralize the reaction mixture to a pH level of approx. 5 to 7, after which toluene, xylene, methylisobutyl ketone, ether or any other substance that can be separated from water is added as a solvent, if necessary, to separate the water layer and then water-wash the oil layer to obtain the oil layer containing the target substance. Next, if necessary the solvent is distilled away from the obtained oil layer to refine the target substance, after which a crystallization solvent is added to the remaining oil layer to cause crystallization, and then the deposits are filtered out to obtain coarse crystal. If the purity of the coarse crystal is low, the above crystallization process may be repeated once or several times, if necessary, to cause recrystallization.

Next, the new polynuclear polyphenol provided as another aspect of the present invention and which may be derived from the 1,3-bis(3-formyl-4-hydroxyphenyl)adamantane is expressed by general formula (2) below.

[Chemical 9]

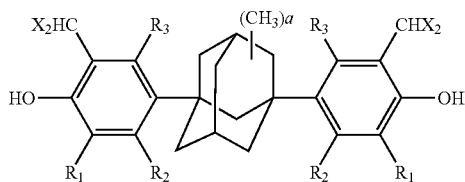

General Formula (2)

In the polynuclear polyphenol expressed by general formula (2) above, a, $R_1$, $R_2$ and $R_3$ are the same as in general formula (1) above, while X represents a hydroxyphenyl group expressed by general formula (3) below. In general formula (3), R represents an alkyl group with 1 to 4 carbon atoms or cycloalkyl group with 5 to 7 carbon atoms, while b is an integer of 1 to 3 and c is an integer of 0 to 4. If c is between 2 and 4, all Rs may be either identical or different, proviso that $1 \leq b+c \leq 5$.

[Chemical 10]

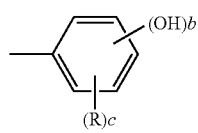

General Formula (3)

Among the possible combinations satisfying the above conditions, a compound where $R_1$ is an alkyl group and at least one of $R_2$ and $R_3$ is a hydrogen atom is preferable, while a compound where both $R_2$ and $R_3$ are a hydrogen atom or only $R_2$ is a hydrogen atom is more preferable. Also, a should preferably be 0.

As for the hydroxyphenyl group expressed by general formula (3), hydroxyphenyl groups having a structure corresponding to "$1 \leq b+c \leq 4$" is preferred. Among these hydroxyphenyl groups satisfying this condition, those expressed by general formula (4) below, where b is 1 and position 4 is substituted, are more preferable.

[Chemical 11]

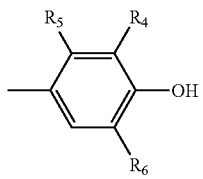

General Formula (4)

(wherein $R_4$, $R_5$ and $R_6$ each represent independently a hydrogen atom, alkyl group with 1 to 4 carbon atoms, or cycloalkyl group with 5 to 7 carbon atoms).

If $R_1$ in general formula (2) is an alkyl group, a hydroxyphenyl group where at least one of $R_4$ and $R_6$ is a hydrogen atom in general formula (4) is more preferred because the reactivity of such hydroxyphenyl group is different from the reactivity of the hydroxyl group of the hydroxyphenyl group bonded to position 1,3 of the adamantane ring in general formula (2).

In other words, specific examples of the polynuclear polyphenol expressed by general formula (2) as proposed by the present invention include, among others, compounds where b is 1 and position 4 is substituted in general formula (3) (that is, compounds having the substituent group shown in general formula (4)). These compounds include the following, among others:

1,3-bis{3-bis(2,5-dimethyl-4-hydroxyphenyl)methyl-5-methyl-4-hydroxyphenyl}adamantane

[Chemical 12]

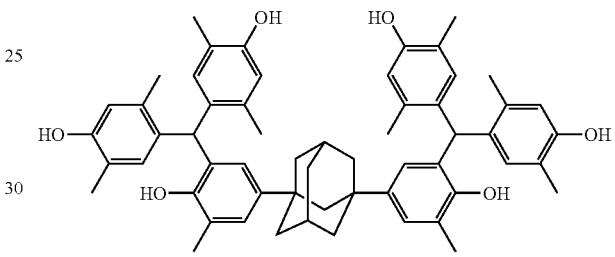

1,3-bis{3-bis(3-methyl-4-hydroxyphenyl)methyl-5-methyl-4-hydroxyphenyl}adamantane

[Chemical 13]

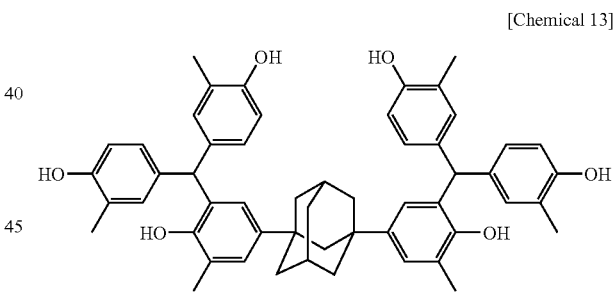

1,3-bis{3-bis(4-hydroxyphenyl)methyl-5-methyl-4-hydroxyphenyl}adamantane

[Chemical 14]

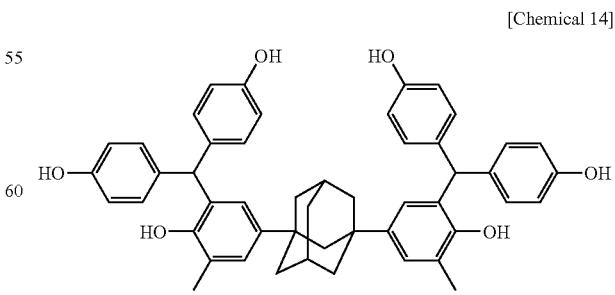

1,3-bis{3-bis(2,3,5-trimethyl-4-hydroxyphenyl)methyl-5-methyl-4-hydroxyphenyl}adamantane

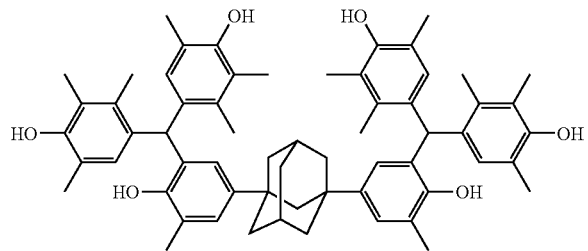

1,3-bis{3-bis(2-methyl-5-cyclohexyl-4-hydroxyphenyl)methyl-5-methyl-4-hydroxyphenyl}adamantane

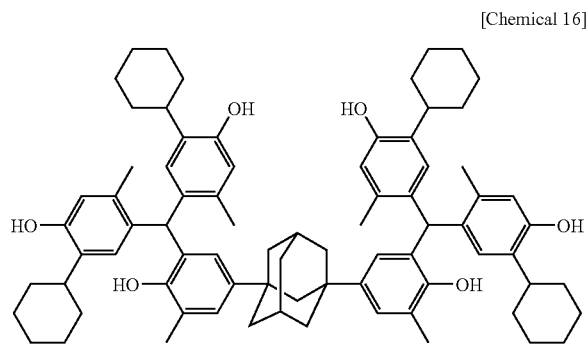

1,3-bis{3-bis(3-ethyl-4-hydroxyphenyl)methyl-5-methyl-4-hydroxyphenyl}adamantane,
1,3-bis{3-bis(3-isopropyl-4-hydroxyphenyl)methyl-5-methyl-4-hydroxyphenyl}adamantane,
1,3-bis{3-bis(3-n-propyl-4-hydroxyphenyl)methyl-5-methyl-4-hydroxyphenyl}adamantane,
1,3-bis{3-bis(3-t-butyl-4-hydroxyphenyl)methyl-5-methyl-4-hydroxyphenyl}adamantane,
1,3-bis{3-bis(3-n-butyl-4-hydroxyphenyl)methyl-5-methyl-4-hydroxyphenyl}adamantane,
1,3-bis{3-bis(3-sec-butyl-4-hydroxyphenyl)methyl-5-methyl-4-hydroxyphenyl}adamantane,
1,3-bis{3-bis(3-isobutyl-4-hydroxyphenyl)methyl-5-methyl-4-hydroxy phenyl}adamantane,
1,3-bis{3-bis(3-cyclohexyl-4-hydroxyphenyl)methyl-5-methyl-4-hydroxyphenyl}adamantane,
1,3-bis{3-bis(4-hydroxyphenyl)methyl-5-isopropyl-4-hydroxyphenyl}adamantane,
1,3-bis{3-bis(3-methyl-4-hydroxyphenyl)methyl-5-isopropyl-4-hydroxyphenyl}adamantane,
1,3-bis{3-bis(2,5-dimethyl-4-hydroxyphenyl)methyl-5-isopropyl-4-hydroxyphenyl}-adamantane,
1,3-bis{3-bis(3-isopropyl-4-hydroxyphenyl)methyl-5-isopropyl-4-hydroxyphenyl}adamantane,
1,3-bis{3-bis(2,3,5-trimethyl-4-hydroxyphenyl)methyl-5-isopropyl-4-hydroxyphenyl}-adamantane,
1,3-bis{3-bis(3-t-butyl-4-hydroxyphenyl)methyl-5-isopropyl-4-hydroxyphenyl}adamantane,
1,3-bis{3-bis(3-sec-butyl-4-hydroxyphenyl)methyl-5-isopropyl-4-hydroxyphenyl}adamantane,
1,3-bis{3-bis(3-isobutyl-4-hydroxyphenyl)methyl-5-isopropyl-4-hydroxyphenyl}adamantane,
1,3-bis{3-bis(3-cyclohexyl-4-hydroxyphenyl)methyl-5-isopropyl-4-hydroxyphenyl}-adamantane,
1,3-bis{3-bis(2-metyl-5-cyclohexyl-4-hydroxyphenyl)methyl-5-isopropyl-4-hydroxyphenyl}-adamantane,
1,3-bis{3-bis(2,5-dimethyl-4-hydroxyphenyl)methyl-2,5-dimethyl-4-hydroxyphenyl}-adamantane,
1,3-bis{3-bis(2-methyl-5-cyclohexyl-4-hydroxyphenyl)methyl-2,5-dimethyl-4-hydroxyphenyl}-adamantane,
1,3-bis{3-bis(2,5-dimethyl-4-hydroxyphenyl)methyl-5-ethyl-4-hydroxyphenyl}adamantane,
1,3-bis{3-bis(2,5-dimethyl-4-hydroxyphenyl)methyl-5-sec-butyl-4-hydroxyphenyl}-adamantane,
1,3-bis{3-bis(2,5-dimethyl-4-hydroxyphenyl)methyl-5-isobutyl-4-hydroxyphenyl}-adamantane,
1,3-bis{3-bis(3-methyl-4-hydroxyphenyl)methyl-5-t-butyl-4-hydroxyphenyl}adamantane,
1,3-bis{3-bis(3-methyl-4-hydroxyphenyl)methyl-5-ethyl-4-hydroxyphenyl}adamantane,
1,3-bis{3-bis(2,5-dimethyl-4-hydroxyphenyl)methyl-4-hydroxyphenyl}adamantane,
1,3-bis{3-bis(3-methyl-4-hydroxyphenyl)methyl-4-hydroxyphenyl}adamantane,
1,3-bis{3-bis(2,3,5-trimethyl-4-hydroxyphenyl)methyl-4-hydroxyphenyl}adamantane,
1,3-bis{3-bis(5-cyclohexyl-2-methyl-4-hydroxyphenyl)methyl-4-hydroxyphenyl}adamantane,
1,3-bis{3-bis(3-ethyl-4-hydroxyphenyl)methyl-4-hydroxyphenyl}adamantane,
1,3-bis{3-bis(3-isopropyl-4-hydroxyphenyl)methyl-4-hydroxyphenyl}adamantane,
1,3-bis{3-bis(3-t-butyl-4-hydroxyphenyl)methyl-4-hydroxyphenyl}adamantane,
1,3-bis{3-bis(3-sec-butyl-4-hydroxyphenyl)methyl-4-hydroxyphenyl}adamantane,
1,3-bis{3-bis(3-isobutyl-4-hydroxyphenyl)methyl-4-hydroxyphenyl}adamantane,
1,3-bis{3-bis(3-cyclohexyl-4-hydroxyphenyl)methyl-4-hydroxyphenyl}adamantane,
1,3-bis{3-bis(4-hydroxyphenyl)methyl-4-hydroxyphenyl}adamantane,
1,3-bis{3-bis(2,5-dimethyl-4-hydroxyphenyl)methyl-4-hydroxy-5-methylphenyl}-4-methyladamantane,
1,3-bis{3-bis(2,5-dimethyl-4-hydroxyphenyl)methyl-4-hydroxy-5-methylphenyl}-5,7-dimethyladamantane,
1,3-bis{3-bis(3-methyl-4-hydroxyphenyl)methyl-5-methyl-4-hydroxyphenyl}-4-methyladamantane,
1,3-bis{3-bis(3-methyl-4-hydroxyphenyl)methyl-5-methyl-4-hydroxyphenyl}-5,7-dimethyladamantane,
1,3-bis{3-bis(2-methyl-5-cyclohexyl-4-hydroxyphenyl)methyl-5-methyl-4-hydroxyphenyl}-4-methyladamantane, and 1,3-bis{3-bis(2-methyl-5-cyclohexyl-4-hydroxyphenyl)methyl-5-methyl-4-hydroxyphenyl}-5,7-methyladamantane Examples of the compound where b is 1 and a position other than position 4 is substituted in general formula (3) include the following, among others:

1,3-bis{3-bis(4,6-dimethyl-2-hydroxyphenyl)methyl-5-methyl-4-hydroxyphenyl}-adamantane

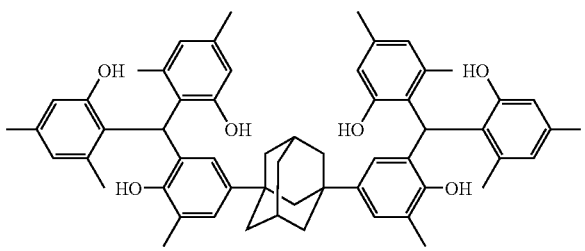

1,3-bis{3-bis(3,4,6-trimethyl-2-hydroxyphenyl)methyl-5-methyl-4-hydroxyphenyl}-adamantane, and 1,3-bis{3-bis(5-methyl-2-hydroxyphenyl)methyl-5-methyl-4-hydroxyphenyl}adamantane Furthermore, examples of the compound where b is 2 or more in general formula (3) include the following, among others:

1,3-bis{3-bis(2-methyl-4,5-dihydroxyphenyl)methyl-5-methyl-4-hydroxyphenyl}adamantane

[Chemical 18]

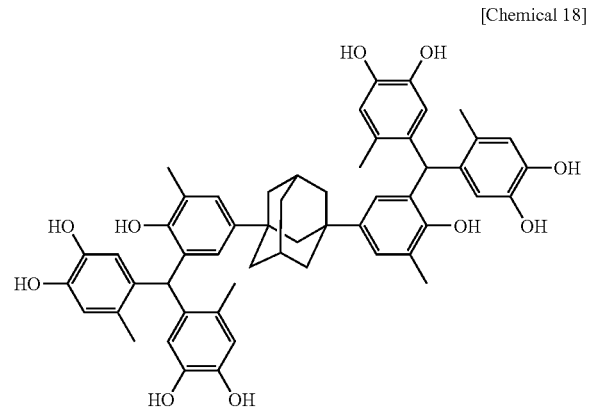

1,3-bis{3-bis(2,3,4-trihydroxyphenyl)methyl-5-methyl-4-hydroxyphenyl}adamantane

[Chemical 19]

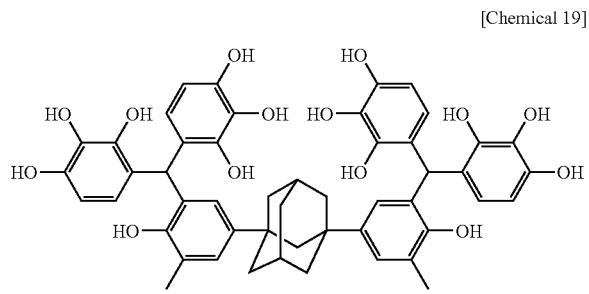

The polynuclear phenol expressed by general formula (2) above as proposed by the present invention is not limited in any way in terms of how it should be produced. A preferred method, however, is one where such polynuclear phenol can be obtained through an industrial process in an easy manner at a good yield and high purity by, for example, causing a 1,3-bis(3-formyl-4-hydroxyphenyl)adamantane expressed by general formula (1) above to react with a phenol in the presence of an acid catalyst such as hydrochloric acid. An example of the reaction formula of this process is given below.

[Chemical 20]

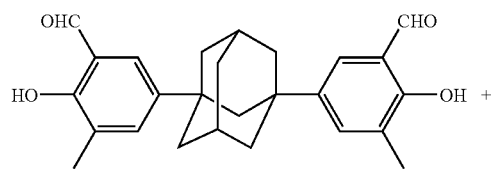

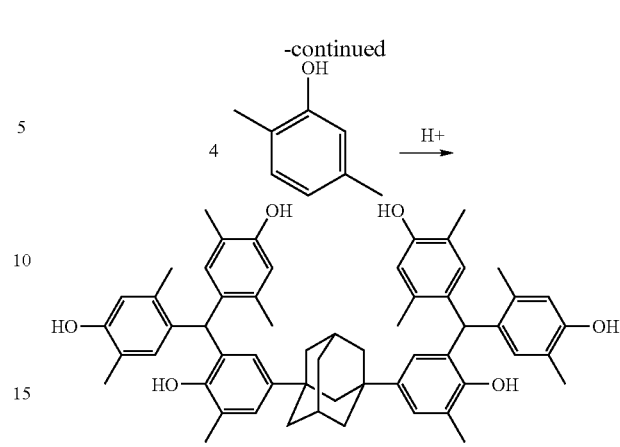

In the polynuclear phenol proposed by the present invention, the phenol, which is the other material to be reacted with the 1,3-bis(3-formyl-4-hydroxyphenyl)adamantane expressed by general formula (1) above, is a phenol corresponding to the hydroxyphenyl group in general formula (3) above expressed by X in general formula (2) above, where at least one of the o-position and p-position in such phenol is not yet substituted with respect to the hydroxide group.

A phenol where the number of substituent groups each constituted by an alkyl group with 1 to 4 carbon atoms or cycloalkyl group with 5 to 7 carbon atoms is 3 or less is preferable in terms of facilitating synthesis, while a phenol whose p-position is not yet substituted is more preferred. In other words, specific examples of the material phenol corresponding to the hydroxyphenyl group shown in general formula (3) above include, for example, phenols where b corresponds to 1 in general formula (3) above. These phenols include the following, among others:

Phenol, o-cresol, p-cresol, m-cresol, 2,5-xylenol, 2,6-xylenol, 3,5-xylenol, 2,3,6-trimethylphenol, 2,3,5-trimethylphenol, 2-cyclohexyl-5-methylphenol, 2-cyclohexylphenol, 2-ethylphenol, 2-t-butylphenol, 2-t-butyl-5-methylphenol, 2,4-xylenol, 2,6-di-t-butylphenol, 2,4-di-t-butylphenol, and 2-sec-butylphenol Also, phenols where b is 2 or more in general formula (3) above include the following, among others:

Resorcin, catechol, hydroquinone, 4-methylcatechol, 3-methylcatechol, 2-methylresorcinol, 4-methylresorcinol, and pyrogallol Among the methods to produce the polynuclear phenol proposed by the present invention, a preferred method is such that the 1,3-bis(3-formyl-4-hydroxyphenyl)adamantane expressed by general formula (1) above is used as a material and this material is caused to react in the presence of an acid catalyst with a phenol corresponding to the hydroxyphenyl group in general formula (3) above expressed by X in general formula (2) above. The ratio of 1,3-bis(3-formyl-4-hydroxyphenyl)adamantane and phenol varies depending on the type of phenol used and it is not possible to set a specific value. Normally, however, this ratio should be in a range of 4:1 to 20:1, or preferably in a range of 4.5:1 to 8:1, as the mol ratio of the phenol to the 1,3-bis(3-formyl-4-hydroxyphenyl)adamantane. Also, an acid catalyst is used in the aforementioned reaction. This acid catalyst is an inorganic acid or organic acid having an acid strength anywhere from strong acidity to mild acidity. To be specific, this acid may be 35% hydrochloric acid, hydrogen chloride gas, sulfuric acid, phosphoric acid or other inorganic acid, or p-toluenesulfonic acid, methanesulfonic acid, oxalic acid or other organic acid. The amount of acid catalyst varies depending on the type of acid catalyst used and it is not possible to set a specific value. Normally, however, the amount of acid catalyst should be in a range of 1 to 100 percent by weight, or preferably in a range of 10 to 30 percent by weight, with respect to the material phenol. Also, a reaction solvent may or may not be used in the reaction.

Preferred reaction solvents include methanol, buthanol and other lower aliphatic alcohols, toluene, xylene and other aromatic hydrocarbons, and methylisobutyl ketone and other aliphatic ketones. If catechol, resorcin or any other material having a high melting point and high solubility in water is used, water can also be used as a reaction solvent.

The amount of solvent is not limited in any way. However, a solvent should preferably be used by an amount in a range of 0.1 to 10 times by weight, or in a range of 0.1 to 2 times by weight in the case of an organic solvent, with respect to the material phenol.

The reaction temperature is normally in a range of 10 to 100° C., or preferably in a range of 20 to 50° C. Under a temperature condition in these ranges, the reaction normally completes in around 1 to 20 hours.

After the reaction has ended, an appropriate amount of ammonia water, sodium hydroxide or other alkali water is added to the obtained reaction mixture in order to neutralize the reaction mixture to a pH level of approx. 5 to 7, after which toluene, xylene, methylisobutyl ketone, ether or any other substance that can be separated from water is added as a solvent, if necessary, to separate the water layer and then water-wash the oil layer to obtain the oil layer containing the target substance. Next, to refine the target substance, as necessary, the solvent and unreacted phenol are distilled away from the obtained oil layer, after which a crystallization solvent is added to the remaining oil layer to cause crystallization, and then the deposits are filtered out to obtain coarse crystal. If the purity of the coarse crystal is low, the above crystallization process may be repeated once or several times, if necessary, to cause recrystallization.

EXAMPLE 1

Synthesis of 1,3-bis(3-formyl-5-methyl-4-hydroxyphenyl)adamantane

Into a 2-liter four-way flask, 615.6 g (5.4 mol) of trifluoroacetic acid was introduced and then the reaction container was replaced with nitrogen, after which 126.0 g (0.9 mol) of hexamethylenetetramine was drip-fed into the reaction container over a period of 1 hour under agitation at room temperature. Next, the temperature was raised to 70° C., and then 104.4 g (0.3 mol) of 1,3-bis(3-methyl-4-hydroxyphenyl)adamantane in powder form was added intermittently over a period of 1 hour by keeping the temperature at the same level. After the entire amount of adamantane had been added, the liquid temperature was raised to 90° C., and this temperature was maintained to cause reaction for 25 hours under agitation.

After the reaction had ended, the temperature of the obtained reaction mixture was lowered to 70° C., and then 210.0 g of water was added to the reaction mixture to cause reaction for 2 hours and 30 minutes under agitation while maintaining the temperature at the same level (crystal precipitated while the mixture was being agitated). After the reaction had ended, 16% aqueous sodium hydroxide solution was added to the obtained reaction mixture in order to neutralize the mixture. The temperature of this neutralized reaction mixture was then raised to 60° C., after which 100 g of acetic acid ethyl ester was added and the mixture was let cool naturally, and then the cooled mixture was filtered to obtain 126.8 g of coarse crystal. Next, the obtained coarse crystal was introduced, along with 1,204.6 g of acetic acid ethyl ester and 150 g of water, into a 2-liter four-way flask, and the flask was heated to 70° C. to dissolve the coarse crystal, after which the water layer was separated and removed and the obtained oil layer was further mixed with water in order to water-wash and separate the oil layer in the same manner as explained above. Next, the solvent was removed from the obtained water-washed oil layer by means of condensation under decompression, and the resulting oil layer was cooled, filtered and dried to obtain the target 1,3-bis(3-formyl-5-methyl-4-hydroxyphenyl)adamantane in the form of 68.2 g of powder crystal having a light yellow color (the crystal had a purity of 95.5% according to the analysis by high-speed liquid chromatography). The yield of the target substance with respect to the 1,3-bis(3-methyl-4-hydroxyphenyl)adamantane was 56.3 mol percent.

Melting point 182.5° C. (peak-top value by differential thermal analysis) Molecular weight 403 (M-H)⁻ (mass spectrometry) Proton nuclear magnetic resonance spectrum (400 MHz, solvent: DMSO-d6, internal standard: tetramethyl silane)

[Chemical 21]

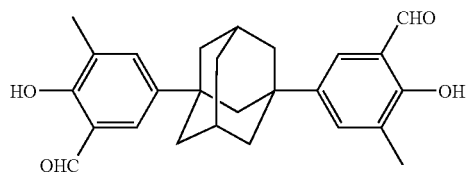

TABLE 1

| Shift value (ppm) | Number of protons | Signal | Assignment |
|---|---|---|---|
| 1.73 | 2 | s | —CH (Adamantane structure) |
| 1.84-1.94 | 10 | m | —CH$_2$ (Adamantane structure) |
| 2.21 | 6 | s | —CH$_3$ |
| 2.25 | 2 | s | —CH$_2$ (Adamantane structure) |
| 7.60 | 4 | s | Ph-H |
| 10.03 | 2 | s | —OH |
| 10.90 | 2 | s | —CHO |

EXAMPLE 2

Synthesis of 1,3-bis{3-di(2,5-dimethyl-4-hydroxyphenyl)methyl-5-methyl-4-hydroxyphenyl}adamantane Into a 500-ml four-way flask, 16.0 g (0.13 mol) of 2,5-xylenol and 16.0 g of methanol were introduced and then the reaction container was replaced with nitrogen, after which 12.8 g of hydrochloric acid gas was blown into the container at a temperature of 30° C. Next, a solution prepared by dissolving 32.8 g (0.27 mol) of 2,5-xylenol in 71.2 g of methanol was drip-fed into the reaction container, after which 32.3 g (0.08 mol) of 1,3-bis(3-formyl-5-methyl-4-hydroxyphenyl)adamantane was added at a temperature of 25° C. over a period of 1 hour and 50 minutes to cause reaction. After the entire amount of adamantane had been added, the temperature was raised to 40° C. to cause further reaction for 3 hours under agitation.

After the reaction had ended, 16% aqueous sodium hydroxide solution was added to the obtained reaction mixture in order to neutralize the mixture. The temperature of this neutralized reaction mixture was then raised to 60° C., after which 137 g of toluene was added and the mixture was condensed at normal pressure and the solvent was distilled away. Then, the obtained condensed mixture was again mixed with toluene, and then the mixture was cooled and filtered to obtain 110.0 g of coarse crystal. Next, the obtained coarse crystal was introduced, along with 120 g of methylisobutyl ketone and 60 g of water, into a 500-ml four-way flask, and the flask was heated to 70° C. to dissolve the coarse crystal, after which the water layer was separated and removed and the obtained oil layer was further mixed with water in order to water-wash and separate the oil layer in the same manner as explained above.

Next, the solvent was removed from the obtained water-washed oil layer by means of condensation at normal pressure, and the resulting oil layer was mixed with toluene, and then cooled, filtered and dried to obtain the target 1,3-bis{3-di(2,5-dimethyl-4-hydroxyphenyl)methyl-5-methyl-4-hydroxyphenyl}adamantane in the form of 36.4 g of powder crystal having a light yellow color (the crystal had a purity of 97.5% according to the analysis by high-speed liquid chromatography).

The yield of the target substance with respect to the 1,3-bis(3-formyl-5-methyl-4-hydroxyphenyl)adamantane was 53.1 mol percent.

Melting point 275.8° C. (peak-top value by differential thermal analysis) Molecular weight 856 (M-H)⁻ (mass spectrometry) Proton nuclear magnetic resonance spectrum (400 MHz, solvent: DMSO-d6, internal standard: tetramethyl silane)

[Chemical 22]

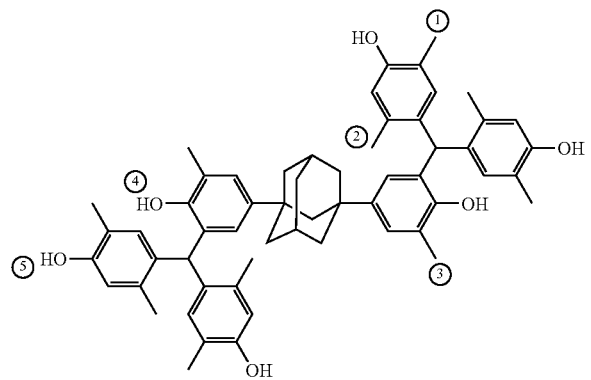

TABLE 2

| Shift value (ppm) | Number of protons | Signal | Assignment |
| --- | --- | --- | --- |
| 1.59-1.66 | 12 | m | —CH, —CH₂— (Adamantane structure) |
| 1.92 | 12 | s | —CH₃ (①) |
| 1.97 | 12 | s | —CH₃ (②) |
| 2.07 | 2 | s | —CH₂— (Adamantane structure) |
| 2.15 | 6 | s | —CH₃ (③) |
| 5.74 | 2 | s | —CH— |
| 6.36 | 4 | s | Ph-H |
| 6.55 | 4 | s | Ph-H |
| 6.56 | 2 | s | Ph-H (Adjacent to an adamantyl group) |
| 6.85 | 2 | s | Ph-H (Adjacent to an adamantyl group) |
| 7.90 | 2 | s | Ph-OH (④) |
| 8.84 | 4 | s | Ph-OH (⑤) |

EXAMPLE 3

Synthesis of 1,3-bis{3-bis(2-methyl-4,5-dihydroxyphenyl)methyl-5-methyl-4-hydroxyphenyl}adamantane Into a 500-ml four-way flask, 15.5 g (0.13 mol) of 4-methylcatechol and 15.5 g of methanol were introduced and then 12.6 g of hydrochloric acid gas was blown into the flask at a temperature of 30° C., after which a solution prepared by dissolving 31.0 g (0.25 mol) of 4-methylcatechol in 69.2 g of methanol was drip-fed into the flask, and then 29.8 g (0.08 mol) of 1,3-bis(3-formyl-5-methyl-4-hydroxyphenyl)adamantane was added at a temperature of 25° C. over a period of 1 hour and 30 minutes to cause reaction. Thereafter, the mixture was caused to react for 5 more hours under agitation at a temperature of 40° C.

Next, 86.1 g of 16% aqueous sodium hydroxide solution was added to neutralize the obtained reaction mixture, and the neutralized reaction mixture was then condensed at normal pressure to remove 83.1 g of solvent. Into the resulting reaction mixture, 120 g of methylisobutyl ketone and 60 g of water were added and the mixture was agitated for 10 minutes, after which the reaction mixture was let stand stationary to separate the water layer and oil layer, with the water layer removed and the oil layer condensed at normal pressure to remove 79.2 g of solvent. Then, 69 g of toluene was added and the resulting mixture was crystallized, cooled and filtered to obtain 55.0 g of coarse crystal. Next, the obtained coarse crystal was introduced, along with 120 g of methylisobutyl ketone and 50 g of water, into a 500-ml four-way flask, and the flask was heated to 70° C. to dissolve the coarse crystal, after which the flask was let stand stationary for 10 minutes to remove the water layer, and then 60 g of water was added further to water-wash and separate the oil layer in the same manner as explained above. Thereafter, the resulting mixture was condensed at normal pressure to remove the solvent and then 120 g of toluene was added. The obtained mixture was crystallized and cooled to 25° C., after which it was filtered and dried to obtain the target 1,3-bis{3-bis(2-methyl-4,5-dihydroxyphenyl)methyl-5-methyl-4-hydroxyphenyl}adamantane in the form of 39.4 g of powder crystal having a white color (the crystal had a purity of 97.4% according to the analysis by high-speed liquid chromatography).

The yield of the target substance with respect to the 1,3-bis(3-formyl-5-methyl-4-hydroxyphenyl)adamantane was 60.7 mol percent.

Melting point 291.8° C. (peak-top value by differential thermal analysis) Molecular weight 864 (M-H)⁻ (mass spectrometry) Proton nuclear magnetic resonance spectrum (400 MHz, solvent: DMSO-d6, internal standard: tetramethyl silane)

[Chemical 23]

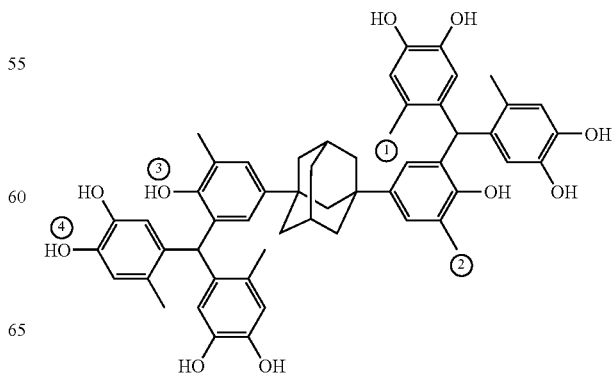

TABLE 3

| Shift value (ppm) | Number of protons | Signal | Assignment |
|---|---|---|---|
| 1.56-1.71 | 12 | m | —CH, —CH$_2$— (Adamantane structure) |
| 1.91 | 12 | s | —CH$_3$ (①) |
| 2.08 | 2 | s | —CH$_2$ (Adamantane structure) |
| 2.15 | 6 | s | —CH$_3$ (②) |
| 5.64 | 2 | s | —CH— |
| 6.15 | 4 | s | Ph-H |
| 6.51 | 4 | s | Ph-H |
| 6.55 | 2 | s | Ph-H (Adjacent to an adamantyl group) |
| 6.87 | 2 | s | Ph-H (Adjacent to an adamantyl group) |
| 7.86 | 2 | s | Ph-OH (③) |
| 8.39 | 8 | s | Ph-OH (④) |

EXAMPLE 4

Synthesis of 1,3-bis{3-bis(2-methyl-5-cyclohexyl-4-hydroxyphenyl)methyl-5-methyl-4-hydroxyphenyl}adamantane Into a 500-ml four-way flask, 57.0 g (0.30 mol) of 5-methyl-2-cyclohexylphenol and 45 g of methanol were introduced and then 10 g of hydrochloric acid gas was blown into the flask at a temperature of 30° C., after which 32.3 g (0.08 mol) of 1,3-bis(3-formyl-5-methyl-4-hydroxyphenyl)adamantane was added under agitation over a period of 1 hour by keeping the temperature at approx. 45° C. to cause reaction. Crystal precipitated while adamantane was being added. After the entire amount of adamantane had been added, the mixture was agitated further at a temperature of approx. 50° C. to cause post-reaction for 18 hours.

After the reaction had ended, 16% aqueous sodium hydroxide solution was added to the obtained reaction mixture in order to neutralize the mixture, after which the temperature of the neutralized reaction mixture was raised to 60° C., and then 36 g of methanol was added. Thereafter, the mixture was cooled and the precipitated crystal was filtered out to obtain 91.3 g of coarse crystal.

The obtained coarse crystal was introduced, along with 170 g of methylisobutyl ketone and 100 g of water, into a four-way flask, and the flask was heated to 75° C. to dissolve the coarse crystal, after which the water layer was separated and removed and the obtained oil layer was further mixed with water to water-wash and separate the oil layer in the same manner as explained above.

Next, 150 g of water and 50 g of methylisobutyl ketone were added to the obtained water-washed oil layer, and the resulting liquid was brought to an azetropic state under normal pressure to distill away methylisobutyl ketone and water. Crystal precipitated during this process. Toluene was then added to the remaining liquid containing this crystal, after which the resulting mixture was cooled and the precipitated crystal was filtered out and dried to obtain the target 1,3-bis{3-bis(2-methyl-5-cyclohexyl-4-hydroxyphenyl)methyl-5-methyl-4-hydroxyphenyl}adamantane in the form of 50.1 g of white powder with a purity of 98.6% (according to the analysis by high-speed liquid chromatography).

The yield of the target substance with respect to the 1,3-bis(3-formyl-5-methyl-4-hydroxyphenyl)adamantane was 74.1 mol percent. Melting point 268.9° C. (peak-top value by differential thermal analysis) Molecular weight 1127 (M-H)$^-$ (mass spectrometry)

Proton nuclear magnetic resonance spectrum (400 MHz, solvent: DMSO-d6, internal standard: tetramethyl silane)

[Chemical 24]

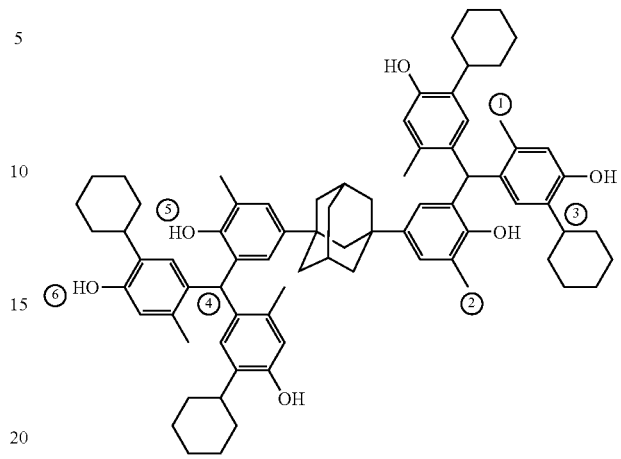

TABLE 4

| Shift value (ppm) | Number of protons | Signal | Assignment |
|---|---|---|---|
| 0.9~1.4 | 20 | m | —CH$_2$— (Cyclohexane ring) |
| 1.5~1.9 | 32 | m | —CH$_2$— (Cyclohexane ring, Adamantane structure) |
| 2.0~2.2 | 2 | m | —CH— (Adamantane structure) |
| 2.12 | 12 | s | —CH$_3$ (①) |
| 2.16 | 6 | s | —CH$_3$ (②) |
| 2.80 | 4 | dd | —CH—(Cyclohexane ring ③) |
| 5.98 | 2 | s | —CH—(④) |
| 6.55 | 4 | s | Ph-H (Cyclohexylphenyl group) |
| 6.75 | 4 | s | Ph-H (Cyclohexylphenyl group) |
| 6.81 | 2 | s | Ph-H (Adjacent to an adamantyl group) |
| 6.85 | 2 | s | Ph-H (Adjacent to an adamantyl group) |
| 8.02 | 2 | s | Ph-OH (⑤) |
| 8.81 | 4 | s | Ph-OH (⑥) |

What is claimed is:

1. A 1,3-bis(3-formyl-4-hydroxyphenyl)adamantane compound expressed by general formula (1) below,

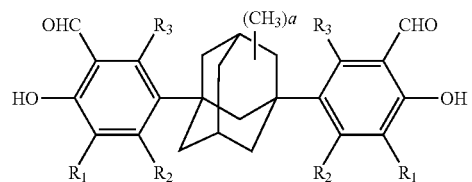

General formula (1)

wherein a represents an integer of 0 to 2, while R$_1$, R$_2$ and R$_3$ each represent independently a hydrogen atom or alkyl group with 1 to 4 carbon atoms.

2. A polynuclear polyphenol compound expressed by general formula (2) below,

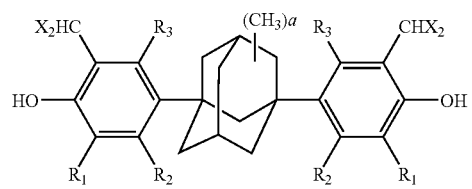

General formula (2)

wherein a, $R_1$, $R_2$ and $R_3$ are the same as in general formula (1), while X represents a hydroxyphenyl group expressed by general formula (3) below; in general formula (3), R represents an alkyl group with 1 to 4 carbon atoms or cycloalkyl group with 5 to 7 carbon atoms, while b is an integer of 1 to 3 and c is an integer of 0 to 4, and if c is between 2 and 4, all Rs may be either identical or different, proviso that $1 \leqq (b+c) \leqq 5$,

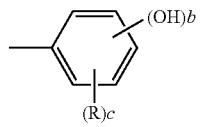

General formula (3).

3. A polynuclear polyphenol compound according to claim 2, wherein X is expressed by general formula (4) below,

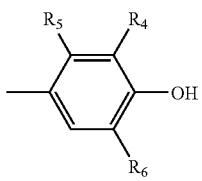

General formula (4)

wherein $R_4$, $R_5$ and $R_6$ each represent independently a hydrogen atom, alkyl group with 1 to 4 carbon atoms, or cycloalkyl group with 5 to 7 carbon atoms.

4. A method for producing 1,3-bis(3-formyl-4-hydroxyphenyl)adamantane compound comprising:
reacting 1,3-bis(4-hydroxyphenyl)adamantane with a hexamethylenetetramine in the presence of an acid to produce a Schiff base; and
hydrolyzing the Schiff base under an acid condition to introduce a formyl group to the 1,3-bis(4-hydroxyphenyl)adamantane.

5. A method for producing a polynuclear phenol represented by general formula (2) comprising:
reacting 1,3-bis(3-formyl-4-hydroxyphenyl)adamantane represented by general formula (1) with a phenol that corresponds to a hydroxylphenyl group represented by general formula (3) in the presence of an acid catalyst,

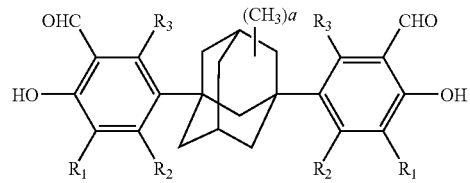

General formula (1)

wherein a represents an integer of 0 to 2, while $R_1$, $R_2$ and $R_3$ each represent independently a hydrogen atom or alkyl group with 1 to 4 carbon atoms,

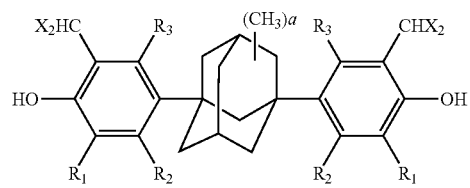

General formula (2)

wherein a represents an integer of 0 to 2, while $R_1$, $R_2$ and $R_3$ each represents independently a hydrogen atom or alkyl group with 1 to 4 carbon atoms, while X represents a hydroxyphenyl group represented by general formula (3) below; and wherein, in general formula (3), R each represents an alkyl group with 1 to 4 carbon atoms or cycloalkyl group with 5 to 7 carbon atoms independently, while b is an integer of 1 to 3 and c is an integer of 0 to 4, and if c is between 2 and 4, all Rs may be either identical or different, proviso that $1 \leqq (b+c) \leqq 5$,

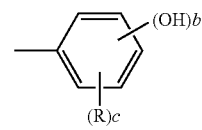

General formula (3).

* * * * *